(12) United States Patent
Zhou et al.

(10) Patent No.: US 9,939,364 B2
(45) Date of Patent: Apr. 10, 2018

(54) TYPE OF TESTING EQUIPMENT FOR DETECTING THE FAILURE PROCESS OF THERMAL BARRIER COATING IN A SIMULTED WORKING ENVIRONMENT

(71) Applicant: Xiangtan University, Xiangtan (CN)

(72) Inventors: Yichun Zhou, Xiangtan (CN); Li Yang, Xiangtan (CN); Zhichun Zhong, Xiangtan (CN); Canying Cai, Xiangtan (CN)

(73) Assignee: XIANGTAN UNIVERSITY, Xiangtan, Hunan (CN)

( * ) Notice: Subject to any disclaimer, the term of this patent is extended or adjusted under 35 U.S.C. 154(b) by 307 days.

(21) Appl. No.: 14/760,444

(22) PCT Filed: Nov. 8, 2013

(86) PCT No.: PCT/CN2013/001357
§ 371 (c)(1),
(2) Date: Jul. 10, 2015

(87) PCT Pub. No.: WO2014/107827
PCT Pub. Date: Jul. 17, 2014

(65) Prior Publication Data
US 2015/0355074 A1    Dec. 10, 2015

(30) Foreign Application Priority Data

Jan. 10, 2013 (CN) .......................... 2013 1 0009293

(51) Int. Cl.
*G01N 3/60* (2006.01)
*G01N 17/00* (2006.01)
(Continued)

(52) U.S. Cl.
CPC .......... *G01N 17/002* (2013.01); *G01M 15/02* (2013.01); *G01N 3/56* (2013.01); *G01N 3/567* (2013.01); *G01N 17/04* (2013.01); *G01N 25/72* (2013.01)

(58) Field of Classification Search
CPC combination set(s) only.
See application file for complete search history.

(56) References Cited

U.S. PATENT DOCUMENTS

| | | | |
|---|---|---|---|
| 9,310,312 B2* | 4/2016 | Jahnke | G01N 21/8851 |
| 2003/0128736 A1* | 7/2003 | Dalio | G01N 25/72 374/141 |

(Continued)

OTHER PUBLICATIONS

English translation of CN101762452.*
English translation of CN102621057.*

*Primary Examiner* — Lisa Caputo
*Assistant Examiner* — Nasir U Ahmed
(74) *Attorney, Agent, or Firm* — U.S. Fairsky LLP; Yue Xu (57) ABSTRACT

A type of testing equipment for detecting the failure process of thermal barrier coating in a simulated working environment; it belongs to the field of simulated special working environment equipment. Testing equipment includes testing platform equipped with static or dynamic specimen holding apparatus, simulated module of working environment, real-time detection module, control panel. This invention is capable of simulating a high temperature, erosive, corrosive working environment for thermal barrier coated turbine blade of aero-engines; simulate high speed spinning working environment for thermal coated blade, simulate static working environment for guiding blade; perform real-time testing of temperature field, 3-D displacement field, crack initiation and expansion, surface oxidation, etc. This invention has achieved complete integration of high temperature, erosive, (Continued)

corrosive working environment for thermal barrier coating and complete integration static or dynamic working environment, complete integration of simulated working environment and real-time testing, thus providing a crucial testing platform and reference data to properly understand the failure mechanism of thermal barrier coated blade and to improve relevant designs; strong applicability.

6 Claims, 4 Drawing Sheets

(51) Int. Cl.
*G01N 25/72* (2006.01)
*G01N 17/04* (2006.01)
*G01N 3/56* (2006.01)
*G01M 15/02* (2006.01)

(56) References Cited

U.S. PATENT DOCUMENTS

2009/0312956 A1* 12/2009 Zombo ................ F01D 5/288
702/34
2012/0320372 A1* 12/2012 Troy .................... G01N 29/043
356/237.2

* cited by examiner

TYPE OF TESTING EQUIPMENT FOR DETECTING THE FAILURE PROCESS OF THERMAL BARRIER COATING IN A SIMULTED WORKING ENVIRONMENT

BACKGROUND OF THE INVENTION

Field of the Invention

This invention pertains to a testing device that detects real-time failure of thermal barrier coating in a simulated working environment. More specifically, this is about turbine blade of aero-engines in a simulated dynamic or static working environment with high temperature, corrosive, erosive conditions. This is a testing device that performs simultaneous testing of thermal barrier coating's failure under a particular working environment. This is a device that creates a special simulated working environment.

Description of Related Art

An aero-engine is regarded as the "heart" of an airplane, it bears crucial importance to the development of aviation industry. The key parameter of an aero-engine is its thrust-weight ratio. Taking the 1st generation F86 fighter and 4th generation F22 fighter as examples, thrust-weight ratio has grown from less than 2 to greater than 10. Obviously, raising aero-engine's thrust-weight ratio is an inevitable trend and required measure in improving engine's performance and efficiency. As thrust-weight ratio improves, temperature of fuel gas inlet continues to rise as well, in the case of 4th generation fighter jets, fuel gas inlet temperature has reached 1700° C. Such significant increase of temperature at fuel gas inlet certainly demands higher requirements on the materials for high temperature components namely turbine blades. In order to meet the requirements of turbine blades, a number of countries have introduced a series of superalloy materials capable of withstanding extreme heat. Currently, nickel-base single crystal superalloys can withstand up to 1150° C., it's needless to say simply using high temperature alloy martial can no longer satisfy the urgent demand of advancing aero-engines. Back in 1953, NASA had already proposed thermal barrier coating, which was to cover the surface of base component with ceramic materials capable of withstanding high temperature as an effort to reduce working temperature on the surface and improve engine's heat efficiency. Once this concept was introduced, it had attracted high level of attentions from defense departments, academics and research institutions all over the world. In efforts of advancing aero-engines in USA, Europe and China, thermal barrier coating technology has all been classified as a crucial technology to high performance aero-engines. The consensus is that thermal barrier coating is currently the most practical approach to significantly increase working temperature of aero-engines.

Thermal barrier coating is generally made up of a ceramic layer for heat insulation, a base metal for bearing mechanical loading, and a transitioning layer for strengthening the bonding between the ceramic and base plus oxidation layer formed during the process of manufacturing and operation. Thermal barrier coating coated blade is generally a shelled body that is cooled by coolant inside shelled body, exterior surface of thermal barrier layer could reach 1100° C. up to 1700° C., surface temperature of alloy material for the base could also reach 700° C. or higher. During actual course of operation, thermal barrier coating could often fail or break due to crack, spall off, separation from interface. There are many causes contributing to failure and breaking of thermal barrier coating. Other than inherent reasons like complex geometric shapes, microscopic structure and performance difference between each layer. The most critical part is that thermal barrier coatings operate in an extreme harsh environment characterized by complex conditions of high temperature, force and chemical coupling. Such strenuous working environment includes: (1) extensive time of high temperature. Thermal barrier coating in extensive time of high temperature would lead to interface oxidation, creep deformation, heat fatigue and phase transformation; (2) Regarding high temperature chemical corrosion, fuel used in aviation turbine engine contains impurities such as Na, S, P, and V. These impurity elements cause chemical reaction and become deposited on high temperature components in the form of $Na_2SO_4$; therefore the application of thermal barrier coating often has to deal with the challenges of various sulfate related corrosion issues; (3) erosion from hard solid pellets, during the course of aero-engine's operation, impacts from hard solid pellets are inevitable thus resulting in erosion. Erosive pellets are generally formed inside the engine or carbon pellets generated during combustion process or pellets formed out of worn-off engine components. Considering thermal barrier coating's complex geometric structure, sophisticated coupling effect of heat, force and chemistry, it is not practical to take the traditional approach of tensile, bending, heat fatigue, thermal stress to conduct research. Back in the 70's, NASA had applied thermal barrier coating on J-75 turbine engine for testing to verify heat insulation effect of thermal barrier coating. The results were used for modifying the material composition of ceramic layer. However, testing on actual aero-engines requires tremendous manpower and resources. Therefore, if we could develop a technology that can simulate the complicated working environment of thermal barrier coating and to perform real-time or root-position non-destructive detection of damages formed from temperature field, strain field, deformation, surface topography, ignition and expansion of cracks during the course leading to failure as real-time observation of damage forming during preparation or operation, it is then possible to properly understand its failure behavior, predict working life and offer direct reference in improving the design and application safety.

Regarding testing devices pertain to simulating working environment of thermal barrier coating and detection of failure: Chen Lai-Fei and his team had introduced simulation method and device for testing heated materials used on aero-engines (Patent number: CN1546974A), that device was to combine sub-sonic speed wind tunnel and material testing camera, silicon nitride and silicon carbide ceramic were combined and used as lining of combustion chamber to enhance combustion chamber's capacity in withstanding high temperature, its specimen holder+transmission chain+rotating lever could all simulate thermal shock. Zhou Hong and his team had introduced a thermal shock testing device for thermal barrier coating (Patent number: CN1818612). Heating and cooling processes were conducted on the coated surface and the surface of metallic base specimens. It could more realistically simulate the working conditions of thermal barrier coated components. Gong Shen-Kai and his team introduced a device simulating working environment of thermal barrier coatings and a method controlling the simulated environment (Patent number: CN1699994). The device is able to simultaneously raise, maintain and reduce temperature and mechanical loading on thermal barrier coating coated hollow cylinder specimens. It is also able to monitor temperature distribution, expansion of interface cracking on a real-time basis. In our earlier work, a testing device was introduced that offered simulation and real-time testing of failure of high temperature component (Patent number: 201010000151). It was able to simulate heat fatigue working environment caused by recurring changes in temperature found on static state high temperature component inside high performance aero-engines. It could perform real-time testing on damaging level via non-contact reactive testing system, acoustic emission non-destructive detection system, alternating current impedance spectroscopy spectrum monitoring system. Nevertheless, with respect to simulating working environment, these devices could only simulate thermal fatigue of thermal barrier coatings, thermal shock or certain single loading working environment with a simple heat and force coupling effect, but not able to achieve simulating high temperature corrosive and erosive condition found in the working environment of thermal barrier coating. Needless to say these devices failed to simulate working environment with a high-speed spinning condition for thermal barrier coating coated turbine blade. With respect to real-time testing of the failure process, only Gong Shen-Kai and our earlier work managed to achieve acoustic emission testing, impedance spectroscopy spectrum testing of interface oxidation, but these non-destructive detection system did not form an integrated unit with the device. These devices also did not have software performing simultaneous control of various non-destructive testing system and could not offer integrated display, record and analysis of various non-destructive testing data. This invention pertains to a testing device that detects real-time failure of thermal barrier coating in a simulated working environment. More specifically, this is about turbine blade of aero-engines in a simulated dynamic or static working environment with high temperature, corrosive, erosive conditions. This is a testing device that performs simultaneous testing of thermal barrier coating's failure under a particular working environment. This is a device that creates a special simulated working environment.

SUMMARY OF THE INVENTION

In order to resolve issues mentioned above, this invention offers a testing device that simulates working environment for thermal barrier coatings and detects real-time failure. This testing device manages to simulating high temperature, erosive, and corrosive condition for thermal barrier coating coated turbine blades at spinning state and actual working condition for guiding vanes at static state. This device integrates multiple non-destructive detection system that performs real-time detection of temperature field, strain field, surface topography, damage evolvement, interface topography on thermal barrier coating in various working environments so that better understanding of damaging mechanism of thermal barrier coating can be reached and reliable assessment and effective solution for improving design could be realized.
Technological Plans Adopted by this Invention are:
A type of testing device for detecting real-time failure of thermal barrier coatings in a simulated working environment, this device consists of 5 parts:
(1) testing platform includes specimen holding apparatus for spinning module used in simulating the working condition of thermal barrier coating coated turbine blade and static working module used in simulating the working condition of thermal barrier coating coated vanes, testing operation platform, specimen compartment;

(2) working environments simulation module includes high temperature flame torch for stimulating high temperature fatigue, temperature gradient, erosive and corrosive condition on thermal barrier coating coated turbine blade, erosive and/or corrosive pellet feeding system, corrosive air delivery duct;
(3) non-destructive detection module includes a temperature collection system, a contact-free 3-D deformation detection system, an acoustic emission non-destructive detection system, an impedance spectroscopy testing system, and high-speed CCD camera system;
(4) cooling system includes a cooling system for thermal barrier coating specimens and a recirculating cooling system for the device;
(5) control and display panel for testing and non-destructive detection system;

The main structural component of the device is divided into two parts: the testing unit and the control display unit. Testing platform, working environment module, non-destructive detection module and cooling system together make up the testing unit. Control and display modules for testing and non-destructive detection system together form the control display unit. The functional components of the device are: holding apparatus that could achieve high-speed spinning or holding apparatus for static state testing, is installed in the middle of the testing platform. Holding apparatus for spinning test is made up by a high-speed spinning motor, an spinning axle (one end of the axle is connected to motor), specimen holder (installed at the other end of the axle) and fastening device; holding apparatus for static state testing is made up by an installation axle equipped with a scale marking engraved plate and a specimen holder of rotating plate and fastening device. Sealed specimen compartment is formed by axle, specimen, specimen holder and fastening device enclosed by quartz glasses. Both sides of specimen compartment have interior and exterior positioning boards to support movement rail and a fastening device for torch simulating the working environment of thermal barrier coatings is installed on movement rail. On one side of the holder inside specimen compartment, multiple fastening devices for thermal couple are installed. On one sidewall of the specimen compartment, a small opening is prepared for installing electrodes and waveguide of acoustic emission detection system. Outside of specimen compartment, multiple CCD cameras are installed. The top of specimen compartment is connected to a dust collection and dehumidification system. Testing operation platform has pellet recycling system. Underneath the testing operation platform has storage area for various non-destructive detection systems.

Specimen holding apparatus described here has 2 types, namely dynamic state and static state. At the dynamic state, specimen is fastened to the spinning axle by fastening devices, a motor powers the spinning axle to spin the specimen fastened to the axle, spinning speed range is 0-12000 r/min; static state specimen holding apparatus includes a plate that could rotate around the center axle and the fastening device that fasten the plate on the center axle, specimen is fastened on the rotating plate, rotating plate and center axle has scale marking engraved, holding angle of the specimen could be adjusted 0-360°. The plate has specimen holders for flat shape, cylinder and turbine blade with thermal barrier coating thus making it possible to conduct test on thermal barrier coating specimen of various shapes.

Working environment simulation module described here includes 2 customized heating torches that are fastened to the testing operation platform via fastening devices and its movement along the rail is powered by a dedicated motor, the torch has a cooling duct built inside and is cooled by recycling water. Flame produced by the torch could reach 3000° C., the distance between the torch and specimen could be adjusted to achieve heating range between 20-1700° C.

Erosive pellet feeding system for working environment module described here is mounted at the pellet duct inside heating torch. Erosive pellets are shot out of torch nozzle by compressed air, high temperature would heat up the pellets of 10-500 μm in diameter to 20-1700° C. and propel them to move toward specimen surface at the speed of 0-250 m/s from random angles.

The corrosive working environment module of the working environment module described here is made possible by 2 ways. One is based on using corrosive pellets delivered through a dedicated duct to the torch nozzle and react with high temperature flame or air to achieve high temperature corrosion with erosive effect; the other one relies on using corrosive air delivered via a dedicated duct inside the torch to the specimen compartment. Corrosive air pressure inside the specimen compartment is 1-6 atm.

Based on the spinning or static state of the working environment, temperature collection system of non-destructive detection module is separated into infrared thermometers and thermocouples. This includes thermocouples, infrared temperature transducer and temperature collection software. For static state testing, the thermocouple described here is a Type B 1600° C. platinum-rhodium thermocouple. A static state experiment tests specimen's temperature at 6 locations including surface, interior duct, cooling air outlet, so as to test thermo barrier effect and temperature of assigned spots; dynamic state test uses an infrared thermometer to test specimen's temperature on surface, interior passage, cooling air outlet;

The non-contact 3-D deformation testing system of the non-destructive detection module described here is based on an ARAMIS non-contact 3-D deformation system. The entire system is integrated inside the testing chamber. A CCD camera was placed outside of the specimen chamber. The control system of the device is able to directly control testing software of ARAMIS non-contact 3-D deformation online testing system and it is used for real-time testing and analysis of specimen's displacement field, strain field and stress field.

The acoustic emission non-destructive detection system of the non-destructive detection module described here is a $10^{-8}$ cm sensitive class PCI-2 acoustic emission non-destructive detection system. The entire system is integrated and installed inside the testing chamber while its transducer, waveguide are connected to specimens through small opening of a specimen compartment. The control system of the device could directly control testing software of PCI-2 acoustic emission non-destructive detection system, thus achieving real-time testing and analysis of crack initiation and propagation in the tested specimen.

The impedance spectroscopy monitoring system of non-destructive detection module described here is a 1260+1296 impedance spectroscopy testing system. It is an integrated system installed inside the device's testing chamber, its testing electrodes are connected through small opening of specimen compartment to the specimen. The control system of the device could directly control testing software of 1260+1296 impedance spectroscopy spectrum testing system, making it possible to perform real-time testing of interface oxidation, damage evolvement and corrosive failure on thermal barrier coating specimen.

The high-speed CCD camera described here is an AVT Manta G-504 high-speed camera system of 500 mega pixel resolution, maximum speed is 9 fps/s. It is an integrated system and installed inside the testing chamber with its CCD camera placed outside the specimen compartment. The device can directly control the testing software of the AVT Manta G-504 high-speed camera system, making it possible to take real-time photos of specimen (6) surface topography.

Cooling system described here has two cooling methods: one is based on air cooling of specimens. Cooled air from the air compressor flow into cooling duct of specimens through the inlet at the bottom and discharged out of the outlet at the top; the other method relies on water cooling of the flame torch using cooling water circulating through flow valves between the water tank and two torches.

The testing control and display platform described here controls all mechanical movements, testing data collections and adjustments, and all testing software of non-destructive detection modules in addition to collecting, recording and displaying testing data. The platform consists of a temperature display, an acoustic emission signal display, an ARAMIS non-contact 3-D deformation test result display, an impedance spectroscopy result display, a high-speed camera display, a testing data display, a progress control switch, a power indicator, an emergency stop switch, a work status indicator, a cooling system control switch, and a cooling system status indicator.

Benefits of this Invention (1) The high temperature fuel torch system that integrates high temperature, corrosive and erosive conditions used in the device describes here is fueled by propane, known for quick rise and fall in temperature. It could reach the working environment required by high temperature components inside aero-engines. Air compressor is used to inject impurities like aluminum, sulfur, phosphorus along with corrosive pellets through erosive pellet feeding system to the torch nozzle and react with high temperature flame, thus forming a strong corrosive air current of hard pellets or combined with corrosive air from corrosive air duct. The combination will simulate a high temperature, corrosive, erosive working environment for thermal barrier coating coated turbine blade. Dual direction feeding based on a symmetrical structure ensures an even distribution on specimen's surface. Mechanical movement device is used to control the distance between the torch nozzle and the surface of a specimen, thus allowing the adjustment of heating area and temperature. Characteristics of feeding system include: wide range of heating temperature, capable of achieving 20-1700° C.; wide range of speed of erosive pellets, capable of achieving 0-250 m/s; wide pressure range of corrosive environment, capable of achieving 1-6 atm. More importantly, the feeding system is able to load up erosive, high temperature and corrosive module simultaneously to simulate complicated heating, mechanical and chemical coupled environments applicable to thermal barrier coating; the 3 modules could also work independently or in the combinations of 2 so it can simulate working environment of only erosion, heat fatigue or thermal impact separately or high temperature oxidation and corrosion; alternatively just high temperature erosion, high temperature corrosion, or erosion and corrosion.

(2) Specimen holding apparatus of this invention includes: dynamic state specimen holding apparatus consisted of a high-speed motor, a spinning axle, a turbine blade holder fastened on the spinning axle and fastening device; a static state specimen holding apparatus consisted of scale marking engraved installation axle, scale marking engraved plate with holders of flat, cylinder specimen and turbine blade and fastening device. For the dynamic state test, specimen on the holding device is fastened to spinning axle, a motor powers the spinning axle to spin the specimen at high speed. A maximum speed could reach 12000 r/min, which is close to actual working speed of thermal coated turbine blade; for static state test, rotating plate has specimen slot of various shapes including flat, cylinder, actual turbine blade shape for placing thermal barrier coating specimen of various shapes and sizes or as blades. By adjusting the angle of the rotating plate to the rotating axle, various angles between the thermal barrier coating specimen and the axle could be achieved, with an adjustable range of 0-360°. This not only simulates the working condition of working blade and guiding vanes at rotating and static states, it also achieves a variety of testing conditions such as erosive angel for thermal barrier coating specimens of various shapes, allowing the analysis of the influence of temperature, pellet angle, speed, geometric shape on the damaging mechanism of thermal barrier coatings.

(3) The non-destructive detection system integrated in the testing device of this invention includes an ARAMIS non-contact 3-D deformation online testing system manufactured by GOM of Germany, a PCI-2 acoustic emission detection system manufactured in USA, a 1260+1296 impedance spectroscopy spectrum testing system manufactured by Solartron of UK, AVT Manta G-504 high-speed camera manufactured by AVT of Germany. These instruments are used for testing 3-D deformation of thermal barrier coating specimens, initiation and propagation of cracks, interface topography evolvement, changes in microscopic structure and chemical composition, interface topography images. Main technological parameters of 3-D deformation online testing are: specimen's surface temperature could reach 2000° C.; the CCD camera resolution is 2448×2050; sampling frequency of real-time data processing is 15-29 Hz; testing range: 0.01%-500%; maximum value of out-of-plane displacement is 140 mm. Main technological parameters of acoustic emission detection system are: the built-in 18-bit A/D converter and processor are more effective in a low amplitude, low threshold (17 dB) setting, maximum signal range is 100 dB, dynamic range >85 dB, 4 high pass and 6 low pass; PCI-2 has an acoustic emission data meter capable of transmitting acoustic emission wave length to hard drive, transmitting speed could reach 10M/s; PCI-2 board has 2 adjustable index channels, which have a 16-bit A/D converter of a speed of 10000 counts/s, multiple FGPA processors and an ASIC IC chip. Main technological parameters of impedance spectroscopy spectrum testing are: electric current range is 200 nA-2 A; electric current resolving power is 1 pA; voltage range is ±14.5V; voltage resolving power is 1 μV; frequency range is 10μ~1 MHz. Main technological parameters are: maximum speed 9 fps/s, resolution is 2452×2054.

(4) There are two types of cooling devices in the testing device mentioned in this invention. The first one is based on using a cooling system for high temperature holding apparatus. Cooling is done by flowing cooling water. The second type is for specimen equipped with a cooling duct and cooling is done by bypassing cooled air. Taking a hollow turbine blade coated with thermal barrier coating as an example, the bottom of turbine blade is machined to add screw threads so that cooling duct could be connected. Cooled air is injected into the duct for cooling, this is to ensure the interior surface of the blade is maintained at predetermined temperature, thus forming a temperature gradient from ceramic surface to the interior surface of the blade. Flow of cooled air is controlled and measured by flow valve. By external connecting to thermal couples, it is possible to record temperatures at 6 different locations on the specimen, namely surface, interior space and cooled air, etc. This offers an effective assessment on the coating's thermal insulation performance.

(5) Various non-destructive detection systems mentioned in this invention are integrated and installed inside the testing chamber. They make up an integrated hardware unit with a working environment simulation module, testing platform and cooling system. Various non-destructive detection systems in action during testing, respective parameters and data storage are controlled by each unit's own testing software. However, each unit's hardware power, software activation and execution status is centrally controlled by the testing device so that simulated working environment testing and real-time detection of failure point are performed simultaneously. Control buttons of testing device, parameters display, temperature display and data, graphics from various non-destructive detection systems are all realized by the display system of the device, thus achieving integrated display of testing parameters and test results.

In regards to all descriptions above, this invention exhibits following features:

a. Capable of simulating high temperature, erosive, corrosive conditions in the working environment of thermal barrier coating coated turbine blade of aero-engines thus realizing integrated simulation of damaging mechanism such as heat fatigue, high temperature corrosion, high temperature erosion. Currently there is no reported patent on such integrated testing device.

b. The device can simulate high-speed spinning state working environment of thermal barrier coating coated turbine blades and static state working environment of guide vanes, achieving integrated simulation of spinning, or static state working environment for thermal barrier coating coated turbine blades. Currently there is no reported patent on such testing device with dynamic state simulation, and much less to say that there is no integrated device capable of achieving both spinning and static state simulations.

c. The device is capable performing real-time testing on temperature field, surface topography evolvement, 3-D deformation field, 3-D displacement field, interface oxidation and its built up rate, initiation and propagation of heat fatigue crack, cooled air flow; achieving the integration of working environment simulation and real-time testing of the failure process. Therefore, the most prominent characteristic of this device is: integrating high temperature, erosive, corrosive condition in working environment of thermal barrier coating, integrating static and dynamic state working environment, integrating working environment simulation and real-time testing, thus offering crucial testing platform and data for better understanding of the damaging mechanism of thermal barrier coating coated turbine blade and improved designs.

d. The device features wide range of working temperature (maximum is 3000° C.) thus making it capable of simulating high temperature components of various fields for heat fatigue failure testing with strong applicability.

BRIEF DESCRIPTION OF DRAWINGS

FIG. 4 is a is relational diagram between the tested high temperature specimen and this invention Figure reference numeral: 1—testing platform; 101—high speed motor; 102—spinning axle; 103—spinning state specimen holder; 104—static state specimen holder; 105—fastening device; 106—installation axle; 107—dust collection system; 108—testing operation platform; 109—specimen compartment; 110—interior fastening board; 111—exterior fastening board; 112—guiding rail; 113—installation device for high temperature torch; 114—thermal couple; 115—fastening device for thermal couple; 116—infrared temperature sensing camera; 117—CCD camera; 2—working environments simulation module; 201—high temperature gas blowtorch; 202—erosive pellet feeding system; 203—corrosive pellet feeding system; 204—fuel gas duct; 205—oxygen duct; 3—non-destructive detection module; 310—non-contact 3-D deformation testing system; 320—acoustic emission non-destructive testing system; 330—impedance spectroscopy testing system; 4—cooling system; 401—air compressor; 402—cooling water tank; 403—flow valve; 404—cooling duct inlet; 405—hollow spinning axle cooling duct inlet; 5—testing and non-destructive detection system; 501—display area; 502—power indicator; 503—work status indicator; 504—cooling system indicator; 505—data collection indicator; 506—movement control switch; 507—torch control switch; 508—synchronous data sampling switch; 509—cooling system switch; 510—emergency switch; 511—power switch; 512—temperature indicator; 513—acoustic emission signal display; 514—impedance spectroscopy display; 515—non-contact 3-D deformation test result display; 6—specimen; 601—waveguide; 602—electrode; 603—cooling duct inlet at the bottom of specimen; 604—cooling duct outlet.

DETAILED DESCRIPTIONS

This invention offers a testing device capable of simulating the working environment of thermal barrier coating and performing real-time analysis of failure. Further details and figures are provided below on actual implementation of the device.

Figure 1:
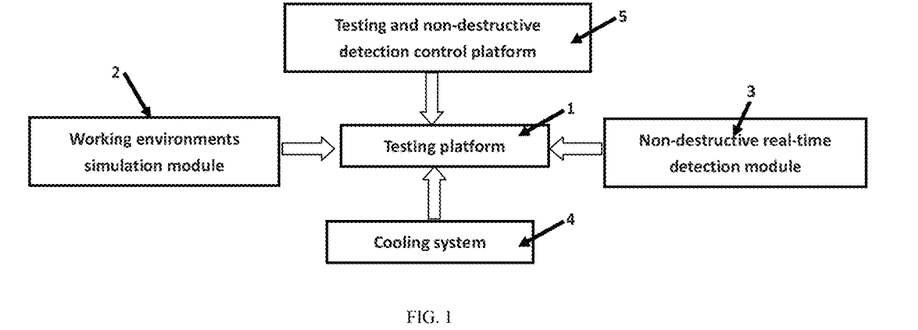
FIG. 1 is an overall schematic conceptual diagram of this invention

As shown in FIG. 1, structural components of this testing device includes: a testing platform, a working environment simulation module, a non-destructive detection module, a cooling system and a non-destructive detection control platform.

Figure 2:
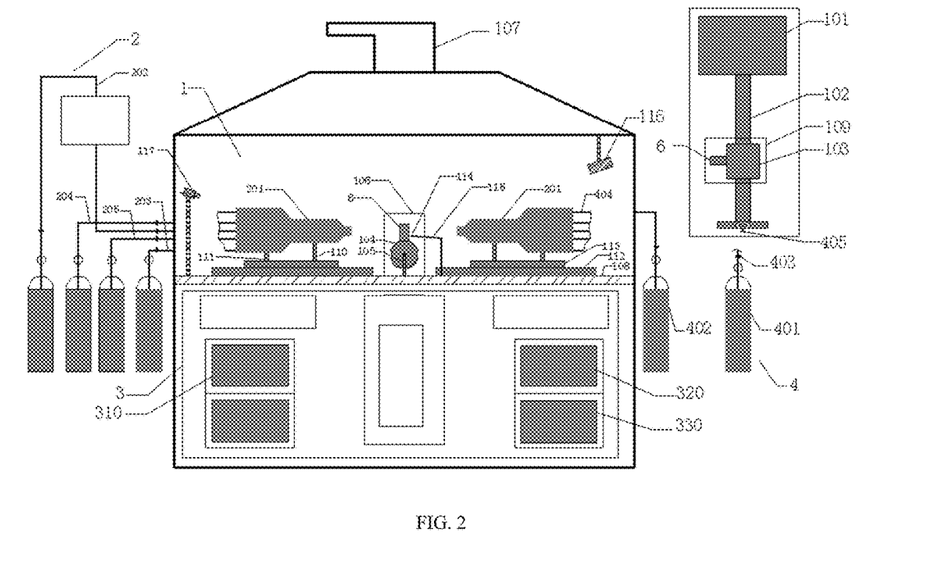
FIG. 2 is a schematic diagram of testing chamber

As shown in FIG. 2, FIG. 2 shows the structural components of this invention. The structure of the testing chamber consists of specimen holding apparatus 1 is installed in the middle of the testing platform, fastening device 105, a high-speed spinning motor 101, a spinning axle 102, a spinning state specimen holder 103; a static state specimen holder 104, installation axle 106 and static state specimen holder 104 engraved with scale marking, the holder could rotate around the axle; position of the entire specimen holding apparatus could be adjusted up or down; in addition to the high-speed spinning motor, specimen holder has quartz glass on each of its surfaces forming an enclosed specimen compartment 109, a dust collection system 107 is connected to the top of specimen compartment, pellet recycle duct is connected through the bottom to testing operation platform 108; both sides of specimen compartment have rails 112 supported by interior fastening board 110 and exterior fastening board 111; installation device 113 of working environments simulation module 2 is installed on rail 112. On one side of static state specimen holder 104 comes with one or more thermocouple fastening devices 115; on one side of specimen compartment 109 comes with a slot for non-destructive detection electrode, waveguide; outside of specimen compartment 109 has multiple CCD cameras 117; an infrared temperature sensing camera 116; underneath testing operation platform 108 is a non-destructive detection system that includes a temperature collection system, a non-contact 3-D deformation detection system 310, an acoustic emission non-destructive detection system 320, an impedance spectroscopy testing system 330, and a high-speed CCD camera system.

Simulation module for thermal barrier coated turbine blade at spinning state is composed of motor 101 powering spinning axle 102, high-speed is optional, one end of spinning axle is specimen 6 fastened by fastening device for spinning motion, speed range is 0-12000 r/min; static state specimen holder 104 includes a plate that could rotate around center axle, specimen is fastened at the plate's radius thus specimen could form an angle between 0-360° with the vertical axle;

High temperature dual direction heating system includes 2 high temperature gas blowtorch 201, heating range is 20-1700° C., torch is fastened by fastening device 113 and movement is controlled by dedicated motor; recirculating water flow inside the torch;

Erosive pellet feeding system is mounted at the pellet duct inside each torch, erosive pellets travelling speed is 0-250 m/s, pellet's diameter is 10-500 μm;

The corrosive working environment module of the working environment module described here is made possible by 2 ways. One is having corrosive pellets delivered through dedicated duct to torch nozzle and react with high temperature flame or air thus achieving high temperature corrosion with erosive effect; Two is having corrosive air delivered via dedicated duct inside the torch to specimen compartment. Corrosive air pressure inside specimen compartment is 1-6 atm.

Figure 3:
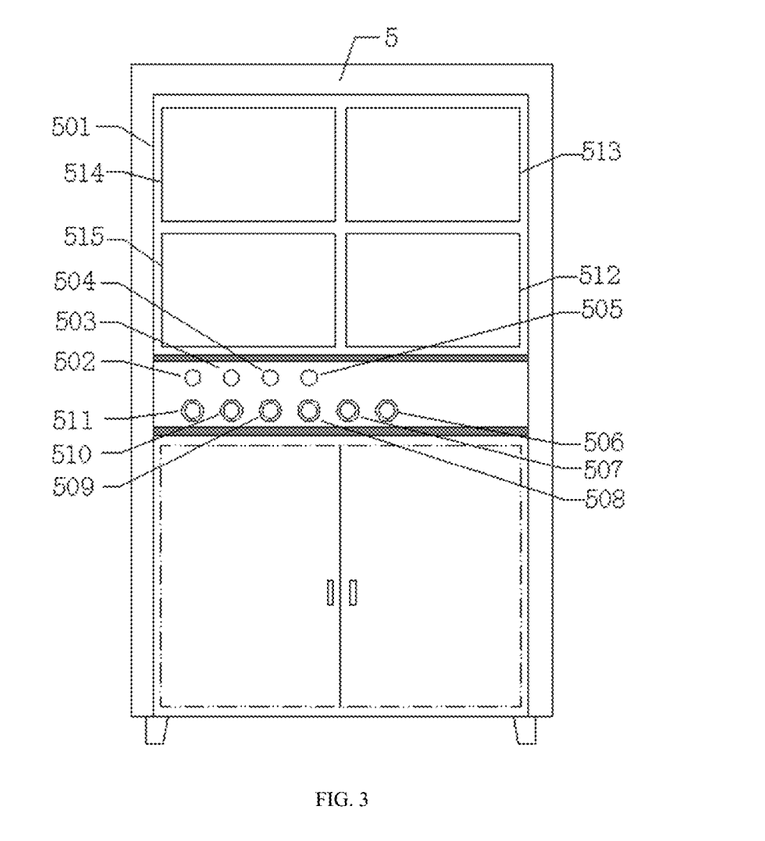
FIG. 3 is a schematic diagram of control chamber

As shown in FIG. 3, FIG. 3 shows the structural components of testing chamber, testing and non-destructive detection system 5 controls and displays all mechanical movements, testing parameter set up, testing data collections. Testing control platform has temperature display 512, acoustic emission signal display 513, impedance spectroscopy spectrum display 514, ARAMIS non-contact 3-D deformation test result display 515, progress control switch 506, 507, power indicator 502, emergency stop switch 510, work status indicator 503, cooling system control switch 509, cooling system status indicator 504.

Figure 4:
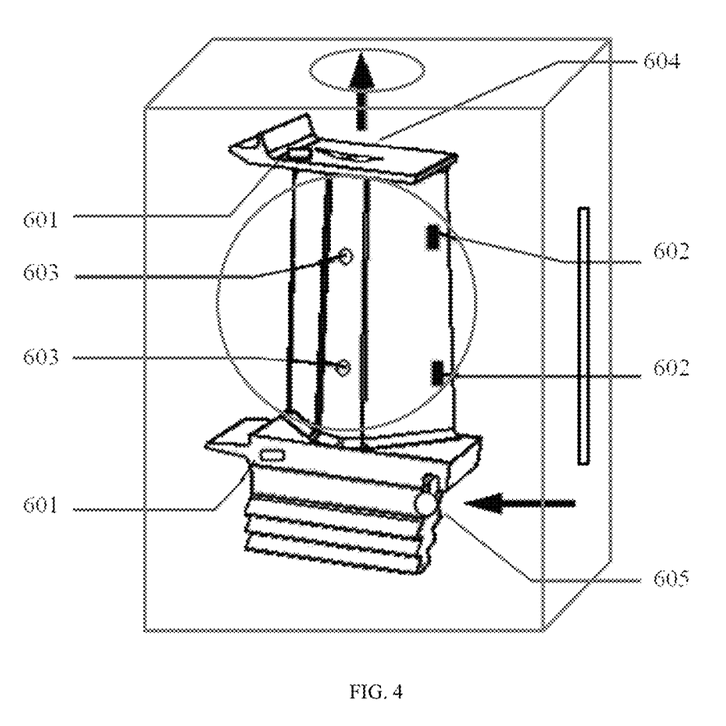

As shown in FIG. 4, FIG. 4 illustrate the connection between tested specimen and this invention. During static state test, temperature collection system includes thermal couple 114, temperature display 512 and temperature collection software. Thermal couple 114 is connected to temperature display 512 at testing control panel. Thermal couple 114 is a B-type 1600° C. platinum rhodium thermal couple that tests temperature at 6 locations namely specimen 6 surface, interior duct, outlet of cooled air, thus achieving temperature testing of designated spots for assessing thermal insulation effect. The 6 thermal couples 114 are placed on testing operation platform 108 via 6 movable thermal couple fastening devices 115, thermal couples 114 are connected to temperature display 512 of testing control platform and computer; cooling air enters cooling duct 405 through cooling water tank 402 and enters via the cooling duct inlet 603 at the bottom of specimen 6, discharge out of cooling duct outlet 604, the system controls and tests the flow of cooling air via flow valve 403; CCD camera 117 is connected to non-contact 3-D deformation detection system 310 and AVT Manta G-504 high-speed camera system; specimen 6 surface has 2 electrodes 602 connected to alternate current impedance spectroscopy testing system 330; both ends of specimen 6 have waveguide 601 welded, waveguides are connected to acoustic emission non-destructive detection system 320.

For testing of thermal barrier coating coated blade or specimen at a spinning state, temperature collection system includes thermal couple 114, infrared temperature sensing camera 116, temperature display 512 and temperature collection software. Thermal couple 114 and infrared temperature sensing camera 116 are connected to temperature display 512 on testing and non-destructive detection system 5. These thermal couples 114 are the same as those used for static state testing but they are used for testing the temperature at the center point of axle connecting hollow spinning axle and specimen, this is to test the temperature of cooling air. Temperature display 512 is placed outside of specimen compartment, periodical testing is done on specimen 6 surface and interior duct by horizontal movement and rotation. Cooling air enters through hollow spinning axle cooling duct inlet 405, passing through cooling water tank 402 and hollow spinning axle 102 to reach cooling duct inlet 603 at the bottom of specimen, cooling air is discharged out of cooling duct outlet g 604 at the top of specimen. The system controls and tests cooling air flow via flow valve; CCD camera is connected to AVT Manta G-504 high-speed camera system.

Cooling system 4 includes air compressor 401, cooling water tank 402, flow valve 403, cooling duct inlet 404, hollow spinning axle cooling duct inlet 405; hollow spinning axle cooling duct inlet 405 and cooling water tank 402 to reach specimen's 6 cooling duct inlet 603 at the bottom, passing through interior duct and discharges out of cooling duct outlet 604 at the top.

Non-contact 3-D deformation testing system 310 is based on a ARAMIS non-contact 3-D online testing system that performs real-time testing and analysis of strain field distribution, stress field distribution and displacement distribution of specimen 6 in a high temperature environment.

Acoustic emission non-destructive detection system 320 is based on a $10^8$ cm sensitivity class PCI-2 acoustic emission non-destructive detection system that detects initiation and propagation of cracks inside the specimen and identifies crack position in various working environments of thermal barrier coating.

Impedance spectroscopy testing system 330 is based on a 1260+1296 impedance spectroscopy spectrum testing system, which performs real-time testing on specimen's interior structure of the thermal barrier coating, initiation of crack and interface oxidation.

CCD camera system is an AVT Manta G-504 high-speed camera system, which performs real-time analysis of the surface topography evolution of thermal barrier coatings.

The procedure of using the testing device mentioned here to conduct static state simulation and real-time testing of thermal barrier coating coated turbine blade is:

Step 1: Specimen preparation: using plasma spray coating techniques to deposit thermal barrier coating on a hollow turbine blade. Composition: bond coating is NiCrAlY alloy, thickness is about 100 μm; ceramic powder material contains 8(wt.)% $Y_2O_3$, ceramic layer is about 300 μm. At the end, a layer of heat-resistant black paint is applied on the surface of the specimen so that the specimen's surface has speckle field of better refection which would be used as attribute speckle field for ARAMIS non-contact 3-D deformation online testing system.

Step 2: Electrodes 602, waveguides 601 used in the test are welded onto the surface of turbine blade specimen and its metallic base at both ends, electrodes 602 and waveguide 601 are connected to impedance spectroscopy testing system 330 and acoustic emission non-destructive detection system 320, respectively. Thermal barrier coating specimen 6 is then fastened to static state specimen holder 104, adjust rotating plate, secure the angle between fastened specimen and vertical axle 4 thermal couples 114 are fastened on the surface of ceramic coated blade, 1 thermal couple is fastened at the cooling duct inlet 603 at the bottom of specimen, 1 thermal couple is fastened at the cooling duct outlet 604 on top. Each thermal couple is connected to temperature collection system, determine if all equipments are working properly.

Step 3: activate ARAMIS non-contact 3-D deformation testing system. Adjust CCD camera 117, confirm target had been marked. Switch on strain testing software, set imagining frequency of ARAMIS testing software to 1 frame per 5 seconds, switch on online automated data storage mode; activate AVT Manta G-504 high-speed camera system. Adjust CCD camera 117, confirm specimen is ready. Switch on testing software, set imagining frequency of AVT Manta G-504 testing software to 1 frame per 5 seconds, switch on online automated data storage mode.

Step 4: Activate acoustic emission non-destructive detection system. Switch on testing software, set up testing parameters; Activate impedance spectroscopy monitoring system, switch on testing software, set testing parameters such as frequency range, voltage.

Step 5: Open up static state specimen holder 104 and switch on cooling water for torch fastening device 113. Open up cooling air valve at the duct inside the turbine blade so cooling air could enter through cooling duct at the bottom of turbine blade, discharge out of top outlet; this forms temperature gradient from ceramic coating surface to interior surface of the metallic base.

Step 6: Activate propane dual direction heating device, activate pellet feeding system, activate corrosive air feeding device (1-3 working environment available), adjust flow of fuel gas, temperature maintained at 1000° C. after 8-10 seconds. Heat up turbine blade from both firection through controlling mechanical movement, temperature rise at about 100° C./s, so surface temperature is maintained at 1000° C. for 10 minutes. In this case, every heating cycle involves a 10-second heating, kept for 300 seconds, cooling for 200 seconds, heating cycle is set at 500.

Step 7: Turn on simulation testing and real-time detection systems to perform real-time testing and recording changes in the temperature field, the 3-D deformation field, 3-D displacement, surface topography of ceramic coating, acoustic emission signals, interface oxidation and coating spallation.

Step 8: After simulation testing is done, experimental data is analyzed and organized to understand the failure mechanism and predict risk area of thermal barrier coating.

The procedure of using the testing device mentioned here to conduct dynamic state simulation and real-time testing on thermal barrier coated turbine blade is:

Step 1: Specimen preparation: using plasma spray coating technique to apply thermal barrier coating material on a hollow turbine blade. Composition: bond coating is NiCrAlY alloy, thickness is about 100 μm; ceramic powder material contains 8(wt.)% $Y_2O_3$, ceramic layer is about 300

μm. At the end, a layer of heat-resistant black paint is applied on the surface of the specimen so that the specimen's surface has speckle field of better refection which would be used as attribute speckle field for ARAMIS non-contact 3-D deformation online testing system.

Step 2: Fasten thermal barrier coated turbine blade specimen 6 on holding apparatus using spinning state specimen holder 103. One thermal couple is fastened at the hollow spinning axle cooling duct inlet 405, testing and non-destructive detection system 116 is fastened outside of specimen compartment 109, thermal couple and infrared thermometer are connected to temperature collection system, determine if all instruments are working properly.

Step 3: activate ARAMIS non-contact 3-D deformation testing system. Adjust CCD camera 117, confirm target had been marked. Switch on strain testing software, set imagining frequency of the ARAMIS testing software to 1 frame per 5 seconds, switch on online automated data storage mode.

Step 4: activate AVT Manta G-504 high-speed camera system. Adjust CCD camera 117, confirm specimen is ready. Switch on testing software, set imagining frequency of AVT Manta G-504 testing software to 1 frame per 5 seconds, switch on online automated data storage mode.

Step 5: Open up static state specimen holder 104 and switch on cooling water for torch fastening device 113. Open up cooling air valve at the duct inside turbine blade so cooling air could enter through cooling duct at the bottom of turbine blade, discharge out of top outlet; this forms temperature gradient from ceramic coating surface to interior surface of metallic base.

Step 6: Activate propane dual direction heating device, activate pellet feeding system, activate corrosive air feeding device (1-3 working environment available), adjust flow of fuel gas, temperature maintained at 1000° C. after 8-10 seconds. Heat up turbine blade from both sides through controlling the mechanical movement, temperature increases at a rate of about 100° C./s, so surface temperature is maintained at 1000° C. for 5 minutes.

Step 7: Switch on high-speed motor spinning system, set spinning speed at 10000 r/min, set spinning time as 5 minutes.

Step 8: Turn on simulation testing and real-time detection systems, thus performing real-time testing and recording of changes in temperature field, 3-D deformation field, 3-D displacement, changes in ceramic coating surface topography, Step 9: After simulation testing is done, testing data is analyzed and organized to determine the failure mechanism and risk area of thermal barrier coating.

This invention is capable of simulating high temperature, erosive, corrosive conditions in the working environment of thermal barrier coating coated turbine blade of aero-engines, thus achieving integrated simulation of multiple damaging process like heat fatigue, high temperature corrosion, and high temperature erosion. It can simulate spinning state working environment for high speed turbine blade as well as static state working environment for guiding blade thus achieving integrated simulation of spinning and static state working environment. It is able to perform real-time testing of temperature field, changes in surface topography, 3-D deformation field, 3-D displacement field, interface oxidation layer and its built up rate, initiation and propagation of heat fatigue cracks, cooling air flow of thermal barrier coatings, thus, achieving integrated working environment simulation and real-time testing of the failure process. This invention realizes integration of high temperature, erosive and corrosive working environment, integration of static and dynamic state working environment, integration of working environment simulation and real-time testing with strong applicability. This invention offers a crucial testing platform and data for better understanding of damaging mechanism of thermal barrier coating and improved designs.

The invention claimed is:

1. A type of testing equipment for detecting a failure process of thermal barrier coating in a simulated working environment, the testing equipment is characterized for having these features:
   1a) testing platform (1), includes specimen holding apparatus for spinning module used in simulating working condition of thermal barrier coating coated turbine blade and static working module used in simulating the working condition of thermal barrier coating coated vanes (101-105), testing operation platform (108), specimen compartment (109);
   1b) working environments simulation module (2), includes high temperature gas blowtorch (201), erosive pellet feeding system (202), corrosive pellet feeding system (203), fuel gas delivery system (204, 205), this environment module simulating high temperature fatigue, temperature gradient, corrosion and erosion in the working environment of thermal barrier coating; the erosive pellet feeding system (202) for testing thermal barrier coated turbine blade is mounted inside pellet duct of the working environments simulation module (2) and the high temperature gas blowtorch (201); achieve the simulating corrosive working environment for thermal barrier coating coated turbine blade is based on using corrosive pellets delivered through duct to torch nozzle to react with high temperature flame or air that create high temperature corrosion with erosive effect;
   1c) non-destructive detection module (3), includes a contact-free 3-D deformation detection system (310), an acoustic emission detection system (320), an impedance spectroscopy testing system (330), a temperature collection system, a high-speed CCD camera system;
   1d) cooling system (4), includes a cooling system for thermal barrier coating specimens and a recirculating cooling system for the equipment;
   1e) control and display panel of testing and non-destructive detection system (5);
a static or spinning specimen holding apparatus is installed on testing equipment's, at a static state, a static state specimen holder (104) is installed on the testing operation platform (108) via installation axle (106) and fastening device (105); installation axle (106) and the static state specimen holder (104) have engraved scale markings, the holding apparatus could rotate around center axle; spinning specimen holding apparatus includes high-speed spinning motor (101), spinning axle (102), spinning state specimen holder (103); position of spinning state specimen holder (103) and the static state specimen holder (104) could be adjusted up or down; in addition to high-speed spinning motor, the specimen holder has quartz glass on each of its surfaces forming an enclosed the specimen compartment (109), dust collection system (107) is connected through top of specimen compartment, pellet recycle duct is connected through the bottom to the testing operation platform (108); both sides of specimen compartment has rail (112) supported by interior fastening board (110) and exterior fastening board (111), installation device (113) of the working environment simulation module (2) is installed on rail (112); on one side of the static state specimen holder (104) comes with one or more thermocouple fastening devices (115); on one side of the specimen compartment (109) includes a slot for non-destructive detection electrode, waveguide of acoustic emission; outside of the specimen compartment (109) include CCD cameras (117); an infrared temperature sensing camera (116); underneath the testing operation platform (108) is non-destructive detection system that includes the contact-free 3-D deformation detection system (310), the acoustic emission non-destructive detection system (320), the impedance spectroscopy testing system (330), temperature collection system.

2. According to the description mentioned in patent claim 1 regarding the type of testing device for detecting real-time failure point of thermal barrier coating in the simulated working environment, its characteristics are found on the testing platform (1) further comprising:

2a) for the module that simulates spinning thermal barrier coating coated turbine blades, its spinning axle (102) is powered by electric motors (101) with spinning specimen (6) being held by the axle, spinning speed range is 0-12000 r/min;

2b) the static state specimen holder (104) is a plate that could spin around the installation axle (106) engraved with scale marking, on the plate is a holder for specimen in slab, cylinder form, and actual turbine blade. The spinning plate could spin around the installation axle engraved with scale marking, this makes 0-360° erosion experiment possible;

2c) the testing platform (1) includes the specimen compartment (109) on top to prevent spill or leakage of erosive, corrosive pellets and corrosive gas;

2d) the testing platform (1) includes non-destructive detection device underneath, inside the specimen compartment (109) has small openings for connection to testing electrode (602), waveguide (601) of acoustic emission detection system.

3. According to the description mentioned in patent claim 1 regarding a type of testing device for detecting failure point of thermal barrier coating in the simulated working environment, its characteristics are found on the working environment simulation module (2) further comprising:

3a) high temperature dual-direction heating system for testing thermal barrier blade includes two custom high temperature gas blowtorch (201) installed on the testing operation platform (108) with fastening device (113). Torch movement is controlled by motor on guiding rail (112), inside the torch is cooling duct, flame projected out of torch could reach 3000° C., by adjusting the distance between torch and the specimen (6), heating temperature range is 20-1700° C.;

3b) the speed of erosive pellets is 0-250 m/s, and the diameter of erosive pellets is 10-500 μm;

3c) the other way to achieve simulating corrosive working environment for thermal barrier coating coated turbine blade is based on having corrosive air delivered through corrosive air duct to specimen compartment; air pressure level of corrosive air inside specimen compartment is 1-6 atm.

4. According to the description mentioned in patent claim 1 regarding the type of testing device for detecting real-time failure point of thermal barrier coating in the simulated working environment, its characteristics are found on the non-destructive detection module (3) further comprising:

4a) there are two ways of temperature detection methods for temperature collection system; one is using thermocouple (114); two is using infrared temperature sensing camera (116); thermocouple and infrared thermometer are connected to the temperature display gauge (512) of the testing and non-destructive detection system (5);

4b) thermocouple (114) described here is a Type B 1600° C. platinum-rhodium thermocouple. A static state experiment tests the specimen's (6) temperatures at 6 locations including surface, interior duct, cooling air outlet, so as to test thermal barrier effect and temperature of assigned spots; dynamic state test uses infrared temperature sensing camera (116) to test the specimen's (6) temperature on surface, interior passage, cooling air outlet;

4c) the 3-D non-contact deformation testing system (310) is based on an ARAMIS non-contact 3-D deformation online testing system. The entire integrated system is located at the non-destructive detection module (3) underneath the testing operation platform (108), with the CCD camera (117) placed outside of the specimen compartment (109);

4d) the acoustic emission non-destructive detection system (320) described here is a 10-8 cm sensitivity class PCI-2 acoustic emission non-destructive detection system. The entire integrated system is located at non-destructive detection module (3) underneath the testing operation platform (108), with its transducers and waveguides (601) are connected through small opening of specimen compartment to the specimen (6);

4e) alternating current of the impedance spectroscopy testing system (330) is a 1260+1296 type impedance spectroscopy testing system. The entire integrated system is located at the non-destructive detection module (3) underneath the testing operation platform (108) with its testing electrode (602) connected through small opening of specimen compartment to the specimen (6);

4f) the high speed CCD camera system described here is based on an AVT Manta G-504 high speed camera system. The entire integrated system is installed at non-destructive detection module (3) underneath the testing operation platform (108) with its CCD camera (117) placed outside of the specimen compartment (109).

5. According to the description mentioned in patent claim 1 regarding the type of testing device for detecting real-time failure of thermal barrier coating in the simulated working environment, its characteristics can be found in the cooling system further comprising:

5a) cooling system described here has two parts, air cooling for the specimen (6) and water cooling for high temperature parts of the device such as the high temperature gas blowtorch (201);

5b) the cooling system (4) comprising an air compressor (401), a cooling water tank (402), flow valves (403), cooling duct inlet (404) and hollow spinning axle cooling duct inlet (405); cooled air enters through the hollow spinning axle cooling duct inlet (405) and the cooling water tank (402) to the bottom section of cooling duct inside the specimen (6), flowing through duct inside specimens and exits out of the gas outlet at the top.

6. According to the description mentioned in patent claim 1 regarding the type of testing device for detecting real-time failure of thermal barrier coating in the simulated working environment, its characteristics are found on the control and display panel of testing and non-destructive detection system further comprising:

6a) the control module described here manipulates all mechanical movements, experimental parameter settings, testing software of non-destructive detection module (3), and experimental data collection, while realizing simultaneous operation of the experimental control module and the non-destructive measurement system;

6b) the display module described here is able to simultaneously display all test data of the testing platform (1) and all test data and graphics of non-destructive detection module (3), while realizing simultaneously display of test parameters and non-destructive detection device.

* * * * *